US010533029B1

United States Patent
Isab et al.

(10) Patent No.: US 10,533,029 B1
(45) Date of Patent: Jan. 14, 2020

(54) ANTICANCER TRANS-DIAMINOPLATINUM(II) COMPLEXES OF SELENONES

(71) Applicant: KING FAHD UNIVERSITY OF PETROLEUM AND MINERALS, Dhahran (SA)

(72) Inventors: Anvarhusein A. Isab, Dhahran (SA); Adam A. A. Sulaiman, Dhahran (SA); Ali Alhoshani, Riyadh (SA); Muhammad Altaf, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 16/134,266

(22) Filed: Sep. 18, 2018

(51) Int. Cl.
C07F 15/00 (2006.01)
A61P 35/00 (2006.01)

(52) U.S. Cl.
CPC .......... *C07F 15/0093* (2013.01); *A61P 35/00* (2018.01)

(58) Field of Classification Search
None
See application file for complete search history.

(56) References Cited

U.S. PATENT DOCUMENTS 5,198,564 A * 3/1993 Qianhuan ........... C07F 15/0093
556/137
2017/0034078 A1 2/2017 Nguyen et al.

OTHER PUBLICATIONS

Altoum et al. Polyhedron 128 (2017) 2-8.*
Saeed Ahmad, et al., "Synthesis, crystal structure and anticancer activity of tetrakis(N-isopropylimidazolidine-2-selenone)platinum(II) chloride", Journal of Molecular Structure, vol. 1152, 2018, pp. 232-236
Sangeeta Yadav, et al., "Synthesis and Reactivity of Selones and Dihaloselones: Complexation of Selones with $d^8$- and $d^{10}$-Metal Ions", European Journal of Inorganic Chemistry, vol. 2017, Issue 3, Apr. 20, 2017, pp. 2968-2979 (Abstract only).
Ali Osman S. Altoum, et al., "Synthesis, structural characterization and cytotoxicity evaluation of platinum(II) complexes of heterocyclic selenones". Polyhedron, vol. 128, 2017, pp. 2-8.
Ali Osman S. Altoum, et al., "Synthesis, characterization and in vitro cytotoxicity of platinum(II) complexes of selenones [Pt(selenone)$_2$Cl$_2$]". Journal of Coordination Chemistry, vol. 70, No. 6. 2017. pp. 1020-1031.
Rohit Singh Chauhan, et al., "Reactivity of dipyrimidyl diselenides with [M(PPh3)4] and 2-pyrimidylchalcogenolates with [MCI2(diphosphine)] (M=Pd or Pt)", Journal of Organometallic Chemistry, vol. 717, 2012, pp. 180-186 (Abstract only).
(Continued)

*Primary Examiner* — Clinton A Brooks
(74) *Attorney, Agent, or Firm* — Oblon, McClelland, Maier & Neustadt, L.L.P.

(57) ABSTRACT

Platinum(II) complexes with various selenones (L) having the general formula $PtL_2(NH_3)_2^{+2} X^{-2}$ are disclosed. The platinum(II) complexes inhibit growth of cancer cells in vitro and are useful for treatment of proliferative disorders such as cancers and/or tumors.

19 Claims, 5 Drawing Sheets

Complex 1

(56) References Cited

OTHER PUBLICATIONS

Jaewon Choi, et al., "Submicro-polymer particles bearing imidazoline-2-selenone: dual mode adsorbents with color-sensing for halogens and mercury ions", Polymer Chemistry, vol. 2, No. 11, Sep. 20, 2011, pp. 2512-2517.
Ralph Puchta, et al., "Quantum Chemical Analysis of the Enantioerisation Mechanism of Complexes of the Type $[M^{II}(XU)_4]F+(M=Pt, Pd, Ni; X=S, Se, Te; U=urea)$", European Journal of Inorganic Chemistry. vol. 2006, Issue 20, Oct. 5, 2006, pp. 4063-4067 (Abstract only).
Dolores Fregona, et al., "Palladium and platinum complexes with N,N-dimethylselenourea". Polyhedron, vol. 15. Issue 15, Aug. 1996, pp. 2523-2533 (Abstract only).
Yan Guosen, et al., "The Method of Determination for the force Constants of General Valence Force Field in Vibration of Large Molecules", Gaodeng Xuexiao Huaxue Xuebao, Chemical Journal of Chinese Universities, vol. 9, No. 7, 1988, pp. 700-705 (with English Abstract).
Alicia Zabokrzycka, et al., "Vibrational spectra of transition metal coordination compounds with thio- and seleno-ligands. XVIII. IR spectra and normal coordinate analysis of palladium(II) and platinum(II) complexes with selenourea", Bulletin De L'Academie Polonaise Des Sciences, Serie Des Sciences Chimiques, vol. 27, No. 5, 1979, pp. 391-407 (Abstract only).
Marek M. Kubicki, et al., "The crystal and molecular structure of tetrakis(selenourea)platinum(II) chloride", Material Science, vol. 3, Nos. 1-2, 1977, pp. 35-38 (Abstract only).
R.D. Hancock, et al., "A linear free-energy relation involving the formation constants of palladium(II) and platinum(II)", Journal of Inorganic and Nuclear Chemistry, vol. 39, Issue 6, 1977, pp. 1031-1034 (Abstract only).
A. V. Nikolaev, et al., "Complexing and extraction of platinum metals by some sulfur- and selenium-containing reagents", Izvestiya Sibirskogo Otdeleniya Akaidemii Nauk SSSR, Seriya Khimicheskikh Nauk, vol. 4, 1970, pp. 60-66 (Abstract only).
V. M. Shul'Man, et al., "Selenourea Complexes of Platinum", Izvestiya Akademii Nauk SSSR, Seriya Khnicheskaya, Institute of Inorganic Chemistry, Siberian Branch of the Academy of Sciences of The USSR, vol. 5, May 1970, pp. 1189-1191.
P.J. Hendra, et al., "The laser Raman and infra-red spectra of some thiourea and selenourea complexes of platinum(II) and palladium(II)", Spectrochimeca ACTA, Part A: Molecular Spectroscopy, vol. 24, Issue 11, Nov. 1968, pp. 1713-1720 (Abstract only).
T. Tarantelli, et al., "Four- and Five-co-ordination in Complexes of Palladium(II) and Platinum(II) with NN'-Disubstituted Thio- and Seleno-ureas", Journal of The Chemical Society [Section] A: Inorganic, Physical, Theoretical, vol. 7, Jan. 1, 1968; pp. 1717-1724.
Claudio Furlani, et al., "N,N'-disubstituted selenoureas as ligands" Inorganic and Nuclear Chemistry Letters, vol. 2, No. 12, 1966, pp. 391-394.

\* cited by examiner

US 10,533,029 B1

ANTICANCER TRANS-DIAMINOPLATINUM(II) COMPLEXES OF SELENONES

STATEMENT OF FUNDING ACKNOWLEDGEMENT

This project was funded by King Fand University of Petroleum and Minerals (KFUPM) under the project number IN141029.

BACKGROUND OF THE INVENTION

Field of Disclosure

The present disclosure relates to trans-diaminoplatinum (II) complexes of selenones with antiproliferative or antitumor activities, the use of the complexes as anti-cancer agents and methods of treating cancer using the complexes.

Description of Related Art

The "background" description provided herein is for the purpose of generally presenting the context of the disclosure. All references cited herein are incorporated by reference. Work of the presently named inventors, to the extent it is described in this background section, as well as aspects of the description which may not otherwise qualify as prior art at the time of filing, are neither expressly or impliedly admitted as prior art against the present disclosure.

The wide spread use of platinum(II) complexes including cisplatin [cis-(Pt(NH$_3$)$_2$Cl$_2$)], carboplatin, and oxaliplatin in cancer chemotherapy [Johnstone et al. Chem. Rev. (2016) 116, 3436-3486; Wheate et al. Dalton Trans, 2010; 39: 8113-8127; Dasari et al. Eur. J. Pharmacol. (2014) 364-378; Wilson et al. Chem. Rev. (2014) 114, 4470-4495; Kalayda, G. V. Cancer Chemotherapy and Pharmacology, 2016, 77, 1103-1124; Reedijk, J. Eur. J. Inorg. Chem. 2009, 1303-1312; Kelland, L (2007) Nat Rev Cancer 7:573; and Ahmad et al Transition Metal Chemistry (2006), 31, 1003-1016] has stimulated considerable interest in the synthesis of many new platinum(II) complexes [Montana et al. Curr. Med Chem. 2009; 16, 2235-60; Gay et al. J. Inorg. Biochem. 142 (2015) 15-27; Intini et al. Inorg. Chem. 56 (2107) 1483-1497; Wang et al. Inorg. Chem., 2016, 55, pp 4519-4528; Cui et al. Inorganic Chemistry 2014 53 (7), 3371-3384; Miles et al. Polyhedron, 108, 23 (2016); Escribano et al. Inorg. Chim. Acta, 394, 65 (2013); Garbutcheon-Singh et al. Dalton Trans., 42, 918 (2013); He, L. Research on Chemical Intermediates, 41, 8725 (2015); Yin et al. J. Inorg. Biochem., 105, 1095 (2011); Lakomska, I. Inorg. Chim. Acta, 362 (2009) 669-681; Hoffmann et al. J. Wietrzyk. J. Coord. Chem., 68, 3193-3208 (2015); and Lyu et al. J. Coord. Chem., 69, 1653-1662 (2016)]. The platinum complexes in clinical use are usually characterized by cis-geometry and at least one ligand that is a good leaving group [Johnston et al. Chem. Rev. (2016) 116, 3436-3486; Wheate et al. Dalton Trans, 2010; 39: 8113-8127; Dasari et al. Eur. J. Pharmacol. (2014) 364-378; Wilson et al. Chem. Rev. (2014) 114, 4470-4495; Kalayda, G. V. Cancer Chemotherapy and Pharmacology, 2016, 77, 1103-1124; Reedijk, J. Eur. J. Inorg. Chem. 2009, 1303-1312; Kelland, L (2007) Nat Rev Cancer 7:573; Ahmad et al. Transition Metal Chemistry (2006), 31, 1003-1016; Montana et al. Curr Med Chem. 2009; 16, 2235-60; and Gay et al. J. Inorg. Biochem. 142 (2015) 15-27]. Several nonfunctional trans-complexes were investigated as anticancer agents and were shown to exhibit remarkable activity particularly against cisplatin-resistant cells [Gao et al. Inorg. Chem. Commun. 9 (2006) 722-726: Zhu et al. Cancer Res; 72, 2012, 790-800; Lovejoy et al. Mol Cancer Ther., 10 (2011) 1709-1719; Wilson et al. Proc. Natl. Acad. Sci. USA. 109 (2012) 11987-92; Kasparkova et al. J. Inorg. Biochem. 153 (2015) 206-210; Tamasi et al. J. Inorg. Biochem., 104, 799 (2010); Bartel et al. J. Biol. Inorg. Chem. 17 (2012) 465-74; Quiroga, A. G. J. Inorg. Biochem. 114 (2012) 106-112; Aris et al. Eur. J. Inorg. Chem. 2009 (2009) 1293-1302; Najajreh et al. J. Med. Chem. 45 (2002) 5189-5195; Ramos-Lima et al. J. Med. Chem. 2006, 49, 2640-2651; Kalinowska-Lis et al. Coord. Chem. Rev. 252 (2008) 1328-1345; Natile et al. Coord. Chem. Rev. 216-217 (2001) 383-410; and Najajreh et al. J. Biol. Inorg. Chem., 10, 722 (2005)]. Among the monofunctional compounds, pyriplatin (cis-[Pt(NH$_3$)$_2$(pyridine) Cl]Cl) [Zhu et al. (2012) and Lovejoy et al. (2011)] and phenanthriplatin (cis-[Pt(NH$_3$)$_2$(pherianthridine)Cl]NO$_3$) [Park et al. (2012)] represent the lead compounds of this type. Although transplatin, trans-[Pt(NH$_3$)$_2$Cl$_2$], does not show anticancer activity, its derivatives are active against cisplatin-resistant cells. The cytotoxic activities of the trans-complexes are greater than those of the corresponding cis-isomers and cisplatin [Najajreh et al. (2002), Ramos-Lima et al. (2006), Kalinowska-Lis et al. (2008), and Natile et al. (2001)]. The mechanism of cytotoxicity of trans-complexes is thought to proceed by the formation of interstrand crosslinks between N7 of guanine of one strand and guanine or cytosine of the opposite strand of a double stranded DNA [Kelland, L (2007) Nat Rev Cancer 7:573; Ahmad et al Transition Metal Chemistry (2006), 31, 1003-1016; Kasparkova et al. Biochemistry, 42, 6321 (2003); and Jamieson et al. Chem. Rev. 99 (1999) 2467-2498]. High rate of interstrand crosslinking caused by the trans-complexes has been suggested to be associated with conformational changes in a double stranded DNA, induced by the heterocyclic ligand in a monofunctional adduct, which facilitate for nation of an interstrand crosslink. High interstrand crosslinking for transplatin analogues in comparison with transplatin may be an important factor responsible for their activity in tumor cells [Kelland, L (2007) and Kasparkova et al. (2003)].

Recently, platinum(II) complexes of various thione and selenone ligands have been synthesized and evaluated for in vitro cytotoxic activity against several human cancer cell lines [Mustafa et al. J. Coord. Chem, 2015, 68, 3511-3524; Mustafa et al. Inorg. Chem. Comm. 2014, 44, 159-163; Altoum et al. J. Coord. Chem. 70 (2017a) 1020-103; and Altoum et al. Polyhedron, 128, 2-8 (2017b)]. Among thione complexes, [Pt(EtImt)$_4$]Cl$_2$ (IC$_{50}$=11 µM Vs 21 µM of cisplatin) and [Pt(Diaz)$_4$]Cl$_2$ (IC$_2$=19.1 µM Vs 22.4 µM of cisplatin) showed higher in vitro cytotoxicity against MCF7 cells [Mustafa (2015) and (2014)]. Among selenone complexes, bis(selenone) derivatives [Altoum et al. (2017a)] were found to be more effective than the tetrakis(selenones) [Altoum et al. (2017b)]. Crystal structures of platinum selenone complexes show a distorted square-planar geometry around the platinum center and the coordination of thiones or selenones in terminal S/Se-bonded modes.

In view of the forgoing, one object of the present disclosure is to provide a new class of platinum(II) complexes having cytotoxic properties against cancer and/or tumors with reduced side effects and methods of their use as anticancer agents.

SUMMARY

According to a first aspect of the invention, the current disclosure relates to a platinum (II) complex having formula PtL$_2$(NH$_3$)$_2$$^{+2}$ X$^{-2}$ of, wherein L has formula A

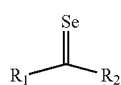

Formula A or a solvate thereof, a tautomer thereof, a stereoisomer thereof, or a mixture thereof; wherein $R_1$ and $R_2$ are independently selected from the group consisting of a hydrogen, $NR_3R_4$, $OR_3$, $SR_3$, $SeR_3$, an optionally substituted alkyl, an optionally substituted alkylene, an optionally substituted cycloalkyl, an optionally substituted aryl, and an optionally substituted arylalkyl; and $R_3$ and $R_4$ are independently hydrogen, an optionally substituted alkyl, an optionally cycloalkyl, an optionally substituted heterocyclyl, an optionally substituted alkyl, and an optionally substituted arylalkyl; or $R_1$ and $R_2$ are linked together forming an optionally substituted ring selected from the group consisting of a four membered ring, a five membered ring, a six membered ring, a seven membered ring, or an eight membered ring; and wherein $X^{-2}$ is a divalent anion or two monovalent anion.

In a preferred embodiment, $R_1$ and $R_2$ are linked together forming an optionally substituted ring.

In another preferred embodiment the ring is saturated or unsaturated cycloalkyl ring or saturated or unsaturated heterocylic ring In another preferred embodiment, the ring is selected from the group consisting of a four membered ring, a five membered ring, a six membered ring, a seven membered ring, or an eight membered ring.

In more preferred embodiment, formula A is selected from the group consisting of formula:

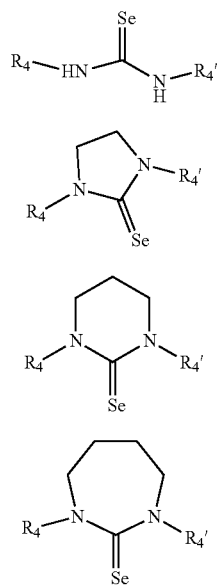

wherein $R_4$ and $R_{4'}$ are independently hydrogen, methyl, ethyl, propyl, isopropyl, butyl, isobutyl, t-butyl, pentyl, isopentyl, phenyl, benzyl.

In another preferred embodiment, $X^{-2}$ is two, nitrate anions.

A second aspect of the invention is directed to a synthetic method for making formula $PtL_2(NH_3)_2^{+2} X^{-2}$ complex of the invention, said method comprising:

(a) mixing an aqueous solution of silver nitrate with an aqueous solution of trans-diaminedihaloplatinum(II) to form silver chloride precipitate,
(b) filtering the precipitated silver chloride and collect the filtrate, and
(c) mixing a solution of a compound of formula A in a solvent miscible with water and the filtrate.

In a preferred embodiment, the trans-diaminedihaloplatinum(II) is selected from the group consisting of trans-diaminedichloroplatinum(II), trans-diaminedibromoplatinum(II), and trans-diaminediiodoplatinum(II).

In a more preferred embodiment, the trans-diaminedihaloplatinum(II) is trans-diaminedichloroplatinum(II).

In another preferred embodiment, the $PtL_2(NH_3)_2^{+2} X^{-2}$ complex precipitates from the reaction mixture.

In a more preferred embodiment, the precipitated $PtL_2(NH_3)_2^{+2} X^{-2}$ is filtered.

A third aspect of the invention is directed to pharmaceutical composition comprising the platinum (II) complex of the invention; and a pharmaceutically acceptable carrier and/or excipient.

In a preferred embodiment, the pharmaceutical composition comprises 0.1-400 μM of the platinum (II) complex relative to the total volume of the composition.

In another preferred embodiment, the pharmaceutical composition comprises pharmaceutically acceptable carrier and/or excipient is at least one selected from the group consisting of a buffer, an inorganic salt, a fatty acid, a vegetable oil, a synthetic fatty ester, a surfactant, and a polymer.

In another preferred embodiment, the pharmaceutical composition further comprises a chemotherapeutic agent.

In a more preferred embodiment, the pharmaceutical composition comprises a platinum (II) complex having a formula selected from the group consisting of

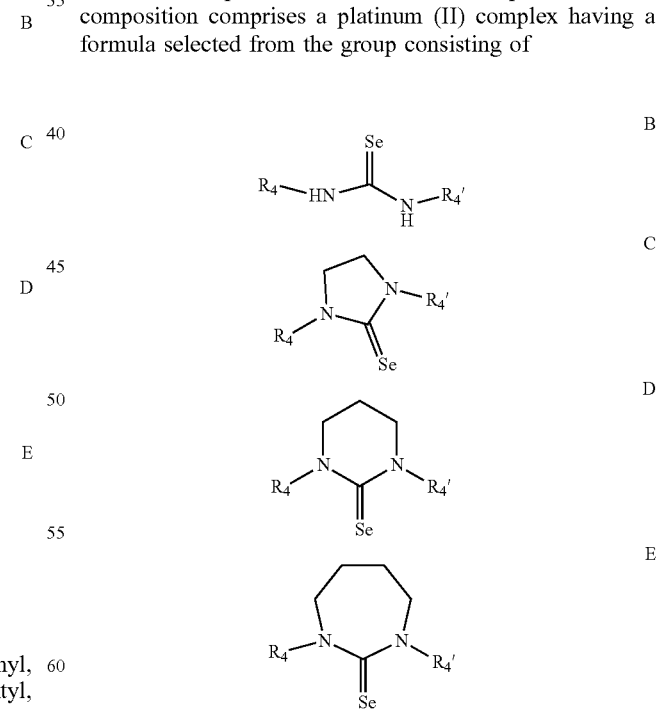

In a most preferred embodiment, the pharmaceutical composition comprises a platinum(II) complex having a formula selected from formula B, C, D, and E, and a chemotherapeutic agent.

A fourth aspect of the intention is directed to a method for treating a proliferative disorder, comprising administering to a subject in need of therapy a sufficient amount of the pharmaceutical composition comprising the platinum(II) complex of the invention, wherein the proliferative disorder is cancer and/or tumor.

In a preferred embodiment, hod comprises administering 1-300 mg/kg of the platinum(II) complex per body weight of the subject.

In another preferred embodiment the method, the subject in need of therapy is having at least one cancer selected from the group consisting of ovarian cancer, cervical cancer, testicular cancer, colon cancer, bladder cancer, breast cancer, non-small cell lung cancer, esophageal cancer, endometrial cancer, head and neck cancer, and osteogenic sarcoma.

In another preferred embodiment of the method, the subject in need of therapy has a central nervous system tumor or a germ cell tumor.

In a more preferred embodiment of the method, the subject is used to treat a mammal.

In a roost preferred embodiment of the method, the subject is human.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Figure 1:
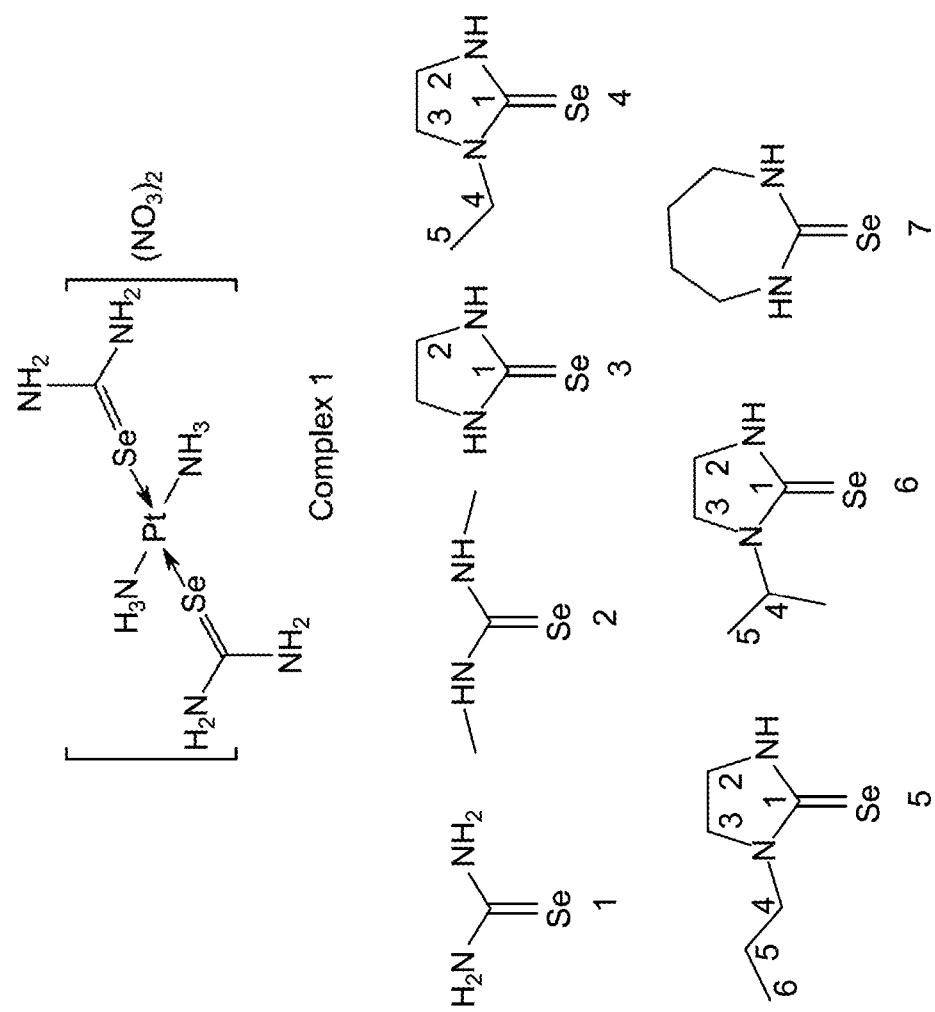
FIG. 1: Chemical structure of complex 1 and selenone ligands 1-7.

Embodiments of the present disclosure will now be described more fully hereinafter with reference to the accompanying drawings, in which some, but not all embodiments of the disclosure are shown.

As used herein, the terms "compound" and "complex" are used interchangeably, and are intended to refer to a chemical entity, whether in a solid, liquid or gaseous phase, and whether in a crude mixture or purified and isolated.

Unless otherwise specified, "a" or "art" means "one or more".

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, isopropanol, n-butanol, isobutanol, tert-butanol, ethyl acetate and other lower alkanols, glycerin, acetone, dichloromethane (DCM), dimethyl sulfoxide (DMSO), dimethyl acetamide (DMA), N,N-dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g. polyethylene glycol (PEG), polypropylene glycol, propylene glycol), and mixtures thereof in suitable proportions. Exemplary solvates include, but are not limited to, hydrates, ethanolates, methanolates, isopropanolates and mixtures thereof. Methods of solution are generally known to those skilled in the art.

As used herein, the term "tautomer" refers to constitutional isomers of organic compounds that readily convert by tautomerization or tautomerism. The interconversion commonly results in the formal migration of a hydrogen atom or proton, accompanied by a switch of a single bond and adjacent double bond. Tautomerism is a special case of structural isomerism, and because of the rapid interconversion, tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), enamine and enamine and anomers of reducing sugars.

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they, are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, and non-enantiomeric optical isomers. Diastereomers seldom have the same physical properties. In terms of the present disclosure, stereoisomers may refer to enantiomers, diastereomers, or both.

Conformers, rotamers, or conformational isomerism refers to a form of isomerism that describes the phenomenon of molecules with the same structural formula but with different shapes due to rotations around one or more bonds. Different conformations can have different energies, can usually interconvert, and are very rarely isolatable. There are some molecules that can be isolated in several conformations. Atropisomers are stereoisomer resulting from hindered rotation about single bonds where the steric strain barrier to rotation is high enough to allow for the isolation of the conformers. In terms of the present disclosure, stereoisomers may refer to conformers, atropisomers, or both.

In terms of the present disclosure, stereoisomers of the double bonds, ring systems, stereogenic centers, metal complexes such as platinum, and the like can all be present in the compounds, and all such stable isomers are contemplated in the present disclosure. Cis- and trans- (or E- and Z-) stereoisomers of the compounds of the present disclosure wherein rotation around the double bond is restricted, keeping the substituents fixed relative to each other, are described. They may be isolated as a mixture of isomers or as separated isomeric forms. S- and R- (or L- and D-) stereoisomers of the compounds of the present disclosure are described and may be isolated as a mixture of isomers or as separated isomeric forms. Also, platinum (II) complexes are known to be square or distorted square planer with the platinum (II) ion at the center. Thus, $PtL_2(NH_3)_2^{+2} X^{-2}$ of the instant invention may be either cis- or trans-complex. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

As used herein, the term "about" refers to an approximate number within 20% of a stated value, preferably within 15% of a stated value, more preferably within 10% of a stated value, and most preferably within 5% of a stated value. For example, if a stated value is about 8.0, the value may vary in the range of 8±1.6, ±1.0, ±0.8, ±0.5, =0.4, ±0.3, ±0.2, or ±0.1.

In this disclosure, the term inert gas refers to any gas that does not react with any component of a reaction mixture of interest. Several inert gases are well-known in the art including nitrogen and nobel gases such as helium and argon.

The present disclosure is further intended to include all isotopes of atoms occurring in the present compounds. Isotopes include those atoms having the same atomic number but different mass numbers. By way of general example, and without limitation, isotopes of hydrogen include deuterium and tritium, isotopes of carbon include $^{13}C$ and $^{14}C$, isotopes of nitrogen include $^{14}N$ and $^{15}N$, isotopes of selenium include $^{74}Se$, $^{76}Se$, $^{77}Se$, $^{77}Se$, and $^{80}Se$, isotopes of oxygen include $^{16}O$, $^{17}O$ and $^{18}O$, and isotopes of platinum include $^{190}Pt$, $^{192}Pt$, $^{193}Pt$, $^{194}Pt$, $^{195}Pt$, $^{196}Pt$, and $^{198}Pt$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

According to a first aspect of the invention, the current disclosure relates to a platinum (II) complex having formula $PtL_2(NH_3)_2^{+2} X^{-2}$, wherein L has formula A

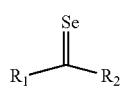

Formula A or a solvate thereof, a tautomer thereof, a stereoisomer thereof, or a mixture thereof; wherein $R_1$ and $R_2$ are independently selected from the group consisting of hydrogen, $NR_3R_4$, $OR_3$, $SR_3$, $SeR_3$, an optionally substituted alkyl, an optionally substituted alkylene, an optionally substituted cycloalkyl, an optionally substituted aryl, and an optionally substituted arylalkyl; and $R_3$ and $R_4$ are independently hydrogen, an optionally substituted alkyl, an optionally substituted cycloalkyl, an optionally substituted heterocyclic, an optionally substituted aryl, and an optionally substituted arylalkyl; or $R_1$ and $R_2$ are linked together forming an optionally substituted ring selected from the group consisting of a four membered ring, a five membered ring, a six membered ring, a seven membered ring, or an eight membered ring, and X is a negatively charged ion or ions.

As used herein, a selone or a selenone is the structural analog of any organic molecule containing a carbonyl group in which the carbonyl oxygen atom is replaced with selenium atom. Without any limitation, examples of selenones are seleno urea $[SeC(NH_2)_2)]$ and derivatives thereof, seleno ketones, seleno aldehydes, selone esters and thio esters, seleno-amides, seleno-peptides, and mono- or diseleno carboxylic acid. Selones are well-known in the art as natural products as well as synthetic products. Both 5-methylaminomethyl-2-selenoueidine and selenoneine, the seleno analog or ergothionine are isolated from organisms [Reich et al. ACS Chem. Biol. (2016) 11, 821-841, which is incorporated herein in its entirety by reference]. Many selenoamides and selenopeptides have been described along with method of their synthesis and characterization [see for example: Toshiaki et al. J. Org. Chem (2015) 80 (13), 6903-6907; Hussain et al. Archives for Organic Chemistry, Volume 2008, Issue 13, pages 129-136; and Vishwanatha et al. J. Org. Chem. (2012) 77 (6), 2689-2702; which are incorporated herein by reference in their entirety]. Taher et al. [Organometallicus (2011) 30 (21), 5943, which is incorporated herein in its entirety by reference] reported the synthesis of mono- and diseleno analogs of carboxylic acids. Anouri et al. [Angew. Chem. Intr. Ed 49, 7530-7533, which is incorporated herein in its entirety by reference] discloses the preparation of the diselenobenzoquinone and indicated the compound is stable. Lyubovskaya et al. [Bull. Acad. Sci. USSR, Div. Chem. Sci (1976) 25 (1), 168-170, incorporated herein by reference in its entirety] disclose the synthesis of 1,3-diseleno-2-selenone, compound A shown below. Also, heterocyclic compound containing the double bonded carbon to selenium are reported in U.S. Pat. No. 6,448,409 which is incorporated herein by reference in its entirety, see in particular the selenium-based cyclocarbamate compound B shown below.

Compound A

Compound B

Schmidt and Silks [Product Class 11: "Seleno and Telluro Carbonic Acid Derivatives" Chapter 11, hi Science of Synthesis: Houben Weyl Method of Molecular Transformation, J. G. Knight, Volum 18, George Thiem Verlag. Publisher (2014); incorporated herein by reference in its entirety]

describe general methodology in the preparation of the selone derivatives of carbonic acid. Seleno urea is often used as a precursor in the synthesis of selenium-containing heterocycles, which may exhibit potential anti-inflammatory and/or antitumor activities. As a result of its electron-donating amino groups, selenourea can also act as an effective ligand for complexation with transition metals.

In a preferred embodiment, $R_1$ and $R_2$ are linked together forming an optionally substituted ring system. The ring system may be a saturated or unsaturated optionally substituted cycloalkyl or heterocyclic of any size. The ring system may be a four membered ring, a live membered ring, a six membered ring, a seven membered ring, or an eight membered ring. The saturated or unsaturated cycloalkyl ring may be a four membered ring, a five membered ring, a six membered ring, a seven membered ring, an eight membered ring or larger. Examples of the cycloalkyl ring systems are cyclobutyl, cyclopentyl, cyclohexyl, cycloheptyl, cyclooctyl, or even larger ring system with or without one or more double or triple bonds. Similarly, the heterocyclic ring system may be saturated or unsaturated of any size having one or more hetero atoms. The heteroatoms may be the same such as nitrogen, oxygen, tellurium, selenium, and sulfur, or different including any combination of heteroatoms such as oxygen, sulfur, tellurium, selenium, or nitrogen. In a more preferred embodiment of the invention, formula A is selected from the group consisting of:

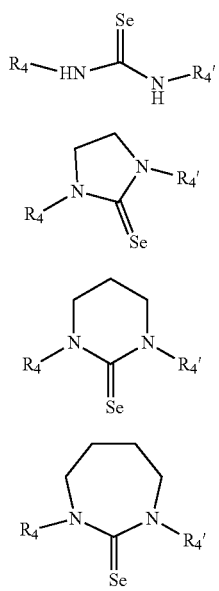

wherein $R_4$ and $R_{4'}$, are independently selected from the group consisting of a hydrogen, an optionally substituted alkyl, au optionally substituted cycloalkyl, an optionally substituted aryl, and an optionally substituted arylalkyl. In a more preferred embodiment, $R_4$ and $R_{4'}$ are independently hydrogen, methyl, ethyl, propyl, isopropyl, butyl, isobutyl, t-butyl, pentyl, isopentyl, phenyl, and benzyl.

As used herein, the term "substituted" refers to at least one hydrogen atom that is replaced with a non-hydrogen group, provided that normal valences are maintained and that the substitution results in a stable compound. When a substituent is noted as "optionally substituted", the substituents are selected from the exemplary group including, but not limited to, halo, hydroxyl, alkoxy, oxo, alkanoyl, aryloxy, alkanoyloxy, amino, alkylamino, arylamino, arylalkylamino, disubstituted amines (e, g. in which the two amino substituents are selected from the exemplary group including, but not limited to, alkyl, aryl or arylalkyl), alkanylamino, aroylamino, aralkanoylamino, substituted alkanoylamino, substituted arylamino, substituted aralkanoylaniino, thiol, alkylthio, arylthio, arylalkylthio, alkylthiono, arylthiono, aryalkylthiono, alkylsulfonyl, arylsulfonyl, arylalkylsulfonyl, sulfonamide (e.g. —SO$_2$NH$_2$), substituted sulfonamide, nitro, cyano, carboxy, carbamyl (e.g. —CONH$_2$), substituted carbamyl (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof and the like.

As used herein, the term "alkyl" unless otherwise specified refers to both branched and straight chain saturated aliphatic primary, secondary, and/or tertiary hydrocarbons of typically $C_1$ to $C_{10}$, preferably $C_1$ to $C_6$, more preferably $C_2$ to $C_3$, and specifically includes, but is not limited to, methyl, trifluoromethyl, ethyl, n-propyl, isopropyl, n-butyl, sec-butyl, isobutyl, t-butyl, pentyl, isopentyl, neopentyl, hexyl, isohexyl, 3-methylpentyl, 2,2-dimethylbutyl, and 2,3-dimethylbutyl.

As used herein, the term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

The term "alkenyl" refers to a straight, branched, or cyclic hydrocarbon fragment containing at least one C=C double bond. Exemplary alkenyl groups include, without limitation, 1-propenyl, 2-propenyl (or "allyl"), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, and 9-decenyl.

The term "alkynyl" refers to a straight or branched hydrocarbon fragment containing at least one C≡C triple bond. Exemplary alkynyl groups include, without limitation, ethynyl, 1-propynyl, 2-propynyl propargyl), 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonynyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, and 9-decynyl.

The term "alkoxy" refers to a straight or branched chain alkoxy including, but not limited to, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy, and decyloxy.

As used herein, the term "aryl" unless otherwise specified refers to functional groups or substituents derived from an aromatic ring including, but not limited to, phenyl, biphenyl, napthyl, anthracenyl, thienyl, and indolyl.

The term "arylalkyl", as used herein, refers to a straight or branched chain alkyl moiety having 1 to 8 carbon atoms that is substituted by an aryl group as defined herein, and includes, but is not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

The term "alkanoyl", as used herein, refers to an alkyl group of specified number of carbon atoms that is bound to an oxygen atom through a double bond. Exemplary alkanoyl groups include, but are not limited to, formyl, acetyl propanoyl, butyryl, and hexanoyl.

The term "aroyl" as used in this disclosure refers to an aromatic carboxylic acyl group includes, for example, benzoyl, 1-naphthoyl, and 2-naphthoyl.

The term "halogen", as used herein, means fluorine, chlorine, bromine, and iodine.

The complex $PtL_2(NH_3)_2^{+2} X^{-2}$ of the invention may be associated with any negatively charged $X^{-2}$ counter ion(s). X may be two monovalent anions such as, but not limited to, fluoride, chloride, bromide, iodide, hydroxide, nitrate, nitrite, mono-basic phosphate, bisulfate, bisulfite, bicarbonate, or carboxylase such as, but not limited to formate, acetate, butyrate, propionate, pentanoate, and hexanoate. In a preferred embodiment, X is two nitrate anions.

Another preferred embodiment of the invention, X is a divalent anion such as sulfate, sulfite, carbonate, phosphate, oxalate, succinate, or tartrate.

In the most preferred embodiment, the selenone ligand is selected from compounds 1-7 shown below.

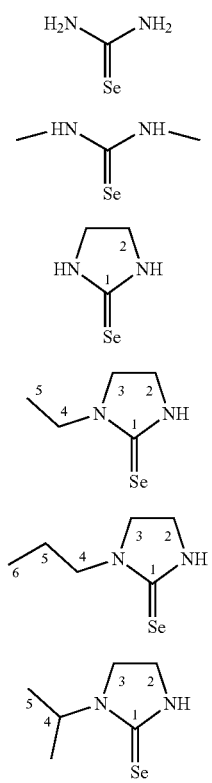

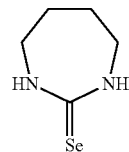

According to a second aspect, the present invention is directed to a synthetic method for making $PtL_2(NH_3)_2^{+2} X^{-2}$ complex of the invention, said method comprising:

(a) mixing an aqueous solution of silver nitrate with an aqueous solution of trans-diaminedihaloplatinum(II) to form silver halide precipitate, (b) filtering the precipitate and collecting the filtrate, and (c) mixing a solution of a compound of formula A in a solvent miscible with water and the filtrate.

In preferred embodiment of the method, a two molar equivalent of aqueous silver nitrate is mixed with a molar equivalent of trans-diaminedihaloplatinum(II) to produce a silver nitrate precipitate. In a more preferred embodiment of the method, the resulting mixture is stirred for a time in the range of 1 to 8 hours, more preferably in the range 2 to 6 hours, in the most preferred embodiment in the range 3 to 4 hours. In a particularly preferred embodiment, the mixture is stirred for 3 hours. The reaction may be carried out at ambient temperature or cooled in an ice bath while mixing and then allow the mixture to warm to ambient temperature. After filtering the precipitated silver halide, the filtrate is mixed with a solution of two molar equivalent of a selenone of formula A in a solvent and the reaction mixture is stirred for a time in the range of 0.5 to 5 hours, preferably in the range 1 to 3 hours, more preferably in the range of 1 to 2 hours, and most preferably for one hour. The solvent may be any organic solvent miscible or partially miscible with water such as, but not limited to, methanol, ethanol, propanol, isopropanol, butanol, isobutanol, acetonitrile, tetrahydrofurane, acetone, dimethylformamide, and dioxane.

In a more preferred embodiment of the method, the trans-diaminedihaloplatinum(II) is selected from the group consisting of trans-diaminedifluroplatinum(II), trans-diaminedichloroplatinum(II), trans-diaminedibromoplatinum (II), and trans-diaminediiodoplatinum(II).

In the most preferred embodiment, the trans-diaminedihaloplatinum(II) is trans-diaminedichloroplatinum(II)

In a more preferred embodiment, the $PtL_2(NH_3)_2^{+2} X^{-2}$ complex precipitates as a colored powder or crystals. Depending on the ligand, it may be any color including, but not limited to colorless, yellow, brown, gray, and black. The yield of the complex is at least 40%, preferably at least 50%, preferably at least 55%, preferably at least 60%, preferably at least 70%, preferably at least 80% by weight, and most preferably at least 90% based on the trans-diaminedichloroplatinum(II) used.

A preferred embodiment of the method further comprises filtering the precipitated trans-$PtL_2(NH_3)_2^{+2} X^{-2}$ complex. The product may be further decolorized, recrystallized and dried by well-known methods in the art. In some instances, it may be desired to exchange the counter ion to another counter ion, which may be carried out by well-known methods in the art such as by the use of ion exchange resins or by chromatography on anion exchange column.

In another preferred embodiment, the product may be separated from the reaction mixture by centrifugation and further purified crystallized by well-known methods in the art.

In some instances, the product $PtL_2(NH_3)_2^{+2} X^{-2}$ complex of the method may be soluble in the reaction mixture and may be isolated and purified by well-known methods in the art including, but not limited to, chromatography and crystallization.

A third aspect of the invention is directed to compositions, in particular, a pharmaceutical composition, wherein the active ingredient is one or more of the $PtL_2(NH_3)_2^{+2} X^{-2}$ complexes of the invention.

As used herein, a "composition" or a "pharmaceutical composition" refers to a mixture of the active ingredient with other chemical components, such as pharmaceutically acceptable carriers and excipients. One purpose of a composition is to facilitate administration of the $PtL_2(NH_3)_2^{+2} X^{-2}$ complex of the invention to a subject. Pharmaceutical compositions of the present disclosure may be manufactured by processes well-known in the art, e.g., by means of conventional mixing, dissolving, granulating, dragee-making, levigating, emulsifying, encapsulating, entrapping or lyophilizing processes. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "active ingredient", as used herein, refers to an ingredient in the composition that is biologically active, for example, the $PtL_2(NH_3)_2^{+2} X^{-2}$ complex wherein L represented by Formula A, a solvate thereof, a tautomer thereof, a stereoisomer thereof, or any mixtures thereof.

In one or more embodiments, the pharmaceutical composition comprises at least 0.01 wt %, 0.05 wt %, 0.1 wt %, 0.5 wt %, 5 wt %, 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 95 wt %, 99 wt %, or 99.9 wt % of the $PtL_2(NH_3)_{2+2} X^{-2}$ complex relative to the total weight of the composition. The pharmaceutical composition may contain 0.1-400 μM, 1-300 μM, preferably 10-200 μM of $PtL_2(NH_3)_2^{+2} X^{-2}$ complex of the invention relative to the total volume of the composition. In some embodiments, the composition comprises up to 0.1 wt %, 1 wt %, 5 wt %, or 10 wt % of a pharmaceutically acceptable salt of the $PtL_2(NH_3)_2^{+2} X^{-2}$ complex. In some embodiments, the composition comprises up to 0.1 wt %, 1 wt %, 5 wt %, or 10 wt % of a pharmaceutically acceptable solvate of the $PtL_2(NH_3)_2^{+2} X^{-2}$ complex. Preferably, the composition may further comprise pharmaceutically acceptable binders, such as sucrose, lactose, xylitol, and pharmaceutically acceptable excipients such as calcium carbonate, calcium phosphate, and dimethyl sulfoxide (DMSO).

In some embodiments, the ability of the active ingredient to reduce the viability of cancer cells may be determined by contacting the pharmaceutical composition with the cancer cells and then performing cell viability assays. Methods of such assays include, without limitation, ATP test, Calcein AM assay, clonogenic assay, ethidium homodimer assay, Evans blue assay, fluorescein diacetate hydrolysis/Propidium iodide staining assay, flow cytometry, Formazan-based assays (MTT, KIT), green fluorescent protein assay, lactate dehydrogenase (LDH) assay, methyl violet assay, propidium iodide assay, Resazurin assay, trypan blue assay, and TUNEL assay. In a preferred embodiment, a MTT assay is used.

In some embodiments, the cancer cells are derived from human cancer cell lines, including, but not limited to, colon cancer cell lines, e.g., HCT15, MDST8, GP5d, HCT116, DLD1, HT29, SW620, SW403 and T84, lung cancer cell lines, e.g., A549, SHP-77, COR-L23/R, and NCI-H69/LX20, breast cancer cell lines, e.g., MDA-MB-231, MCF7, T47D, and VP303, cervical cancer cell Lines, e.g., HeLa DH, HtTA-1, HR5, and C-4I, ovarian cancer cell lines, e.g., A2780, A2780cis, OV7, and PEO23, and skin cancer cell lines, e.g., C32TG, A375, and MCC26. In other embodiments, the cancer cells are collected from a human patient or located in a human patient who is at risk of having, is suspected of having, has been diagnosed with, or is being monitored for recurrence of at least one type of cancer, preferably colon cancer, lung cancer, cervical cancer, testicular cancer, and/or breast cancer. In at least one embodiment, cisplatin-resistant cancer cells are used. These cells may be generated by culturing cancer cells with low doses of cisplatin in order to build their resistance to cisplatin while maintaining cell viability. Examples of cisplatin-resistant cancer cells include, but are not limited to, A549 cisplatin-resistant lung cancer cells, MCF-7 cisplatin-resistant breast cancer cells, A2780cis cisplatin-resistant ovarian cancer cells, and SGC7901cis cisplatin-resistant gastrointestinal cancer cells.

As used herein, the terms "sufficient amount" or "cytotoxic effective amount" are used interchangeably, and are intended to refer to a concentration of the active ingredient that reduces the viability of the cancer cells by at least 5%, 10%, 15%, 20%, 30%, 40%, 50%, 60%, 70%, 80% or 90%, dative to cancer cells not treated with the active ingredient. The reduction in viability may occur no more than 10 days, 7 days, 5 days, 3 days, or 2 days after the active ingredient is contacted with the cancer cells. In one embodiment, the cytotoxic effective amount may be the $IC_{50}$ which is a concentration of the active ingredient which causes the death of 50% of cancer cells in 72 hours (3 days). In one embodiment, the $IC_{50}$ of the $PtL_2(NH_3)_2^{+2} X^{-2}$ complex, the solvate thereof, the tautomer thereof, the stereoisomer thereof, or the mixture thereof against colon cancer cells is in a range of 0.01-150 μM, preferably 1-70 μM, more preferably 30-40 μM. In another embodiment, the $IC_{50}$ of the $PtL_2(NH_3)_2^{+2} X^{-2}$ complex, the solvate thereof, the tautomer thereof, the stereoisomer thereof, or the mixture thereof against lung cancer cells is in a range of 0.01-200 μM, preferably 1-80 μM, preferably 40-50 μM. In another embodiment, the $IC_{50}$ of the $PtL_2(NH_3)_2^{+2} X^{-2}$ complex, the solvate thereof, the tautomer thereof, the stereoisomer thereof, or the mixture thereof against breast cancer cells is n a range of 0.01-120 μM, preferably 1-60 μM, more preferably 40-50 μM.

In some embodiments, other active ingredients in addition to the $PtL_2(NH_3)_2^{+2} X^{-2}$ complex of the current disclosure may be incorporated into a pharmaceutical composition. In one embodiment, the pharmaceutical composition includes a second active ingredient, such as a chemotherapeutic agent or an anticancer agent, for the treatment or prevention of neoplasm, of tumor or cancer cell division, growth, proliferation and/or metastasis in the subject; induction of death or apoptosis of tumor and/or cancer cells; and/or any other forms of proliferative disorder.

As used herein, other non-cancerous proliferative disorders that may also be treated by the currently disclosed pharmaceutical composition include, without limitation, atherosclerosis, rheumatoid arthritis, psoriasis, idiopathic pulmonary fibrosis, scleroderma, cirrhosis of the liver, lymphoproliferative disorder, other disorders characterized by epidermal cell proliferation such as verruca (warts), and dermatitis, and benign proliferative breast disease such as ductal hyperplasia, lobular hyperplasia, and papillomas.

The anticancer agent is at least one of a mitotic inhibitor; an alkylating agent; an antimetabolite; a cell cycle inhibitor; an enzyme; a topoisomerase inhibitor; a biological response modifier; an anti-hormone; an antiangiogenic agent such as MMP-2, MMP-9 and COX-2 inhibitor; an anti-androgen; a platinum coordination complex such as, but not limited to, oxaliplatin, carboplatin; a substituted urea such as hydroxyurea; a methylhydrazine derivative; an adrenocortical suppressant, e.g., mitotane, aminoglutethimide; a hormone and/or hormone antagonist such as the adrenocorticosteriods prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane).

Exemplary anticancer agents include, but are not limited to, alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; anti-microtubule agents including etoposide, vinblastine, vincristine, tenoposide, docetaxel, paclitaxel, vinorelbine, vindesine; cytotoxic antibiotics including daunorubicin, doxorubicin, idarubicin, mitomycin, actinomycin, epirubicin; topoisomerase inhibitors including irinotecan, mitoxantrone, topotecan, and mixtures thereof.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating, agents such as EDTA; sugar alcohols such as mannitol or sorbitol; salt-forming counter ions such as sodium; and/or nonionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatin, vegetable oils, and polyethylene glycols.

In some embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

Exemplary buffers include, without limitation, phosphate buffers, citrate buffer, acetate buffers, borate buffers, carbonate buffers, bicarbonate buffers, and buffers with other organic acids and salts.

Exemplary inorganic salts include, without limitation, calcium carbonate, calcium phosphate, disodium hydrogen phosphate, potassium hydrogen phosphate, sodium chloride, zinc oxide, zinc sulfate, and magnesium trisilicate.

Exemplary fatty acids include, without limitation, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, without limitation, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 34(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltriniethylammonium bromide, tetradecyltrimethylammonium bromide, tetradecyltrimethyl-ammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the composition may be in the form of solid dosage form such as tablets, caplets, capsules, powders, and granules, semi-solid dosage form such as ointments, creams, lotions, gels, pastes, and suppositories, liquid dosage forms such as solutions, and dispersions, inhalation dosage form such as aerosols, and spray, or transdermal dosage form such as patches.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavouring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectable. Dimethyl acetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration may involve the use of transdermal administration such as transdermal patches or iontophoresis devices. Formulation of drugs is discussed in, for example, Hoover, J. E. Remington's pharmaceutical sciences, Mack Publishing Co., Easton, Pa., 1975; and Liberman, H. A.; Lachman, L., Eds. Pharmaceutical dosage forms, Marcel Decker, New York, N.Y., 1980, which are incorporated herein by reference in their entirety.

In other embodiments, the composition having the $PtL_2(NH_3)_2^{+2} X^{-2}$ complex disclosed herein, the solvate thereof, the tautomer thereof, the stereoisomer thereof, or the mixture thereof has different release rates categorized, as immediate release and controlled- or so stained-release.

As used herein, immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to a release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In one embodiment, the composition is not a controlled-release composition.

According to a fourth aspect, the current disclosure relates to a method for treating a proliferative disorder, comprising administering the pharmaceutical composition of the second aspect to a subject in need of therapy.

As used herein, the terms "treat", "treatment", and "treating" in the context of the administration of a therapy to a subject in need thereof refer to the reduction or inhibition of the progression and/or duration of a disease (e.g. cancer), the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such teens may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumour size before administration), or elimination of the cancer cells, (2) inhibiting cancerous cell division and/or cancerous cell proliferation, (3) relieving to some extent (or, preferably, eliminating) one or more symptoms associated with, a pathology related to or caused in part by unregulated or aberrant cellular division, (4) an increase: in disease-free, relapse-free, progression-free, and/or overall survival, duration, or rate (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

The term "subject" and "patient" are used interchangeably. As used herein, they refer to any subject for whom or which therapy, including with the compositions according to the present disclosure is desired. In most embodiments, the subject is a mammal, including but is not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

In one or more embodiments, the proliferative disorder is cancer. In some embodiments, the disclosed method of the fourth aspect is for treating cancer of the blood, brain, bladder, lung, cervix, ovary, colon, rectum, pancreas, skin, prostate gland, stomach, breast, spleen, liver, kidney, head, neck, testicle, bone, bone marrow, thyroid gland, or central nervous system. In a preferred embodiment, the cancer is at least one selected from the group consisting of colon cancer, cervical cancer, breast cancer, and lung cancer. In a more preferred embodiment, the cancer is cervical cancer or breast cancer. In the most preferred embodiment, the cancer is cervical cancer or breast cancer.

As used herein, a subject in need of therapy includes a subject already with the disease, a subject which does not yet experience or exhibit symptoms of the disease, and a subject predisposed to the disease. In preferred embodiments, the subject is a person who is predisposed to cancer, e.g. a person with a family history of cancer. People who (i) had inflammatory bowel disease, or a genetic syndrome such as familial adenomatous polyposis (FAP) and hereditary non-polyposis colorectal cancer (Lynch syndrome), and/or (ii) consumes a low-fiber and high-fat diet are at a higher risk of contracting colon cancer. White women or a person with (i) certain inherited genes (e.g. mutated BRCA1, BRCA2, ATM, TP53, CHEK2, PTEN, CDH1, STK11, and PALB2), (ii) radiation occurred to one's chest, and/or (iii) exposure to diethylstilbestrol (DES) are at a higher risk of contracting breast cancer. People who (i) smoke or regularly breathe in second-hand smoke, (ii) exposed to carcinogens including, but not limited to polycyclic aromatic hydrocarbons (e. g. benzo[a]pyrene, benz[a]anthracene, and methylated derivatives thereof), asbestos, radioactive substances (e.g., uranium, radon), and/or (iii) inhaled chemicals or minerals (e.g., arsenic, beryllium, cadmium, silica, vinyl chloride, nickel compounds, chromium compounds, coal products, mustard gas, and chloromethyl ethers) are at a higher risk of contracting lung cancer.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. Those of ordinary skill in the art are familiar with administration techniques that can be employed with the compounds and methods described herein. In preferred embodiments, the active ingredient and/or the composition described herein are administered orally.

In one or more embodiments, the pharmaceutical composition administered comprises the $PtL_2(NH_3)_2^{+2} X^{-2}$ complex where in L is Formula (A), or a solvate thereof, a tautomer thereof, a stereoisomer thereof, or a mixture thereof, in which $R_1$ and $R_2$ as defined herein.

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", "pharmaceutically effective amount" or sufficient amount refer to that amount of the active ingredient being administered which will relieve to some extent one or more of the symptoms of the disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study. In some embodiments, an effective amount of the platinum(II) complex having the formula $PtL_1(NH_3)_2^{+2} X^{-2}$, wherein L is Formula (A) is in a range of 1-300 mg/kg, preferably 10-200 mg/kg, more preferably 50-100 mg/kg is administered per body weight of the subject.

In treating certain cancers, the best approach is often a combination of surgery, radiotherapy, and/or chemotherapy. Therefore, in at least one embodiment, the pharmaceutical composition is employed in conjunction with radiotherapy. In another embodiment, the pharmaceutical composition is employed with surgery. The radiotherapy and/or surgery may be before or after the composition is administered.

A treatment method may comprise administering a pharmaceutical composition containing the $PtL_2(NH_3)_2^{+2} X^{-2}$ complex of the current disclosure as a single dose or multiple individual divided doses. In some embodiments, the composition is administered at various dosages (e.g. a first dose with an effective amount of 200 mg/kg and a second dose with an effective amount of 50 mg/kg). In some embodiments, the interval of time between the administration of the composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, 5 days, 6 days, or 7 days. In certain embodiments, the composition and one or more additional therapies are administered less than 1 day, 1 week, 2 weeks, 3 weeks, 4 weeks, 1 month, 2 months, 3 months, 6 months, 1 year, 2 years, or 5 years apart.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, 10%, 15%, 20%, 25%, 30%, 40%, 50%, 60%, 70%, 75%, 80%, 85%, 90%, 95%, 99%, or 100%, relative to the tumor size before treatment. In other embodiments, the size of a tumor after treatment does not reduce but is maintained the same as the tumor size before treatment. Methods of assessing tumor size include, but are not limited to, CT scan, MRI, DCE-MRI and PET scan.

In most embodiments, the method further comprises measuring a concentration of a biomarker and/or detecting a mutation in a biomarker before and/or after the pharmaceutical composition comprising the $PtL_2(NH_3)_2^{+2} X^{-2}$ complex of the present disclosure is administered. As used herein, the term "biomarker" refers to a characteristic that is objectively measured and evaluated as an indicator of normal biological processes, pathogenic processes or pharmacological responses to a therapeutic intervention. Generic cancer biomarkers include circulating tumor DNA (ctDNA) and circulating tumor cells (CTC). Exemplary biomarkers for colon cancer include, without limitation, carcinoembryonic antigen (CEA), carbohydrate antigen 242 (CA 242), CA 195, CA 19-9. MSI, and 18qLOH. Exemplary biomarkers for breast cancer include, without limitation, BRCA1, BRCA2, HER-2, estrogen receptor, progesterone receptor, CA 15-3, CA 27.29, CEA, Ki67, cyclin D1, cyclin E, and ERβ. Exemplary biomarkers for lung cancer include, without limitation, CA 125, CA 15-3, EGF receptor, anaplastic lymphoma kinase gene MET, ROS-1, and KRAS. Potentially predictive cancer biomarkers include, without limitation, mutations in genes BRCA1 and BRCA2 for breast cancer and/or ovarian cancer, overexpression of CEA, NSE, CYFRA-21-1, CA-125, and CA-199 for lung cancer, overexpression of TYMS, mutations in genes p53 and KRAS for colon cancer.

The mutation in the biomarker may be detected by procedures such as restriction fragment length polymorphism (RFLP), polymerase chain reaction (PCR) assay, multiplex ligation-dependent probe amplification (MLPA), denaturing gradient gel electrophoresis (DGGE), single-strand confo, illation polymorphism (SSCP), hetero-duplex analysis, protein truncation test (PTT), and oligonucleotide ligation assay (OLA). The procedures to detect the mutation are well-known to those of ordinary skill in the art.

The term "sample" used herein refers to any biological sample obtained from the subject in need of therapy including a single cell, multiple cells, fragments of cells, a tissue sample, and/or body fluid. Specifically, the biological sample may include red blood cells, white blood cells, platelets, hepatocytes, epithelial cells, endothelial cells, a skin biopsy, a mucosa biopsy, an aliquot of urine, saliva, whole blood, serum, plasma, lymph. In some embodiments, the biological sample is taken from a tumor.

The concentration level of the cancer biomarker in a sample may be measured by an assay, for example an immunoassay. Typical immunoassay methods include, without limitation, enzyme-linked immunosorbent assay (ELISA), enzyme-linked immunospot assay (ELISPOT), Western blotting, immunohistochemistry (IHC), immunocytochemistry, immunostaining, and multiple reaction monitoring (MRM) based mass spectrometric immunoassay. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Euro Life Sciences.

In me embodiments, the concentration of the biomarker is measured before and after the administration. When the concentration of the biomarker is maintained, the method may further comprise increasing the effective amount of the $PtL_2(NH_3)_2^{+2} X^{-2}$ by at least 5%, at least 10%, or at least 30%, up to 50%, up to 60%, or up to 80% of an initial effective amount that is in a range of 1-300 mg/kg per body weight of the subject. The increased effective amount may be in a range of 1.05-540 mg/kg, preferably 15-420 mg/kg, more preferably 25-270 mg/kg. The subject may be administered with the increased dosage for a longer period (e.g. 1 week more, 2 weeks more, or 2 months more) than the duration prescribed with the initial effective amount.

In some embodiments, the mutation in the biomarker is detected before administering the composition to identify subjects predisposed to the disease. For example, subjects with a BRCA1 germline mutation are at a higher risk of contracting breast cancers or ovarian cancer. In some embodiments, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration is stopped once the subject is treated.

Having generally described this disclosure, a further understanding can be obtained by reference to certain specific examples which are provided herein for purposes of illustration only and are not intended to be limiting unless otherwise specified.

Example 1

Materials and Methods:
Chemicals:
Transplatin [trans-diamminedichloidoplatinum(II)] was obtained from Strem Chemical Company, USA. Dimethylsulfoxide-$d_6$ and $D_2O$ were purchased from Fluka Chemical Co. Selenourea and N,N'-dimethylselenourea were obtained from Acros Organicl, USA. Other selenone ligands were prepared as previously described [Cristiani et, al. J. Chem. Soc. Perkin Trans. II, (1977) 324; and Wazeer iet al. Magn. Reson. Chem. 2003, 41, 1026-1029 each incorporated by reference in their entirety]. (3-(4,5-Dimethylthiazol-2-yl)-2,5-diphenyltetrazolium bromide, a yellow tetrazole) was purchased from Sigma Chemical Co, St. Louis, Mo., USA.

Cell Cultures:
Solutions of Pt(II) complexes of selenone 1-7 and cisplatin at concentrations of 1.0 µM, 5.0 µM, 10.0 µM, 25.0 µM, and 50.0 µM were prepared in Dulbecco modified eagle medium (DMEM). The human cervical cancer cell line HeLa and human breast cancer cell line MDA-231 were seeded and maintained in quadruplicate in a 96-well tissue culture plate at $5 \times 10^4$ cells per well in 200 µL of the same medium. The cancer cells were incubated for 24 hours before treatment. All compounds were dissolved in 50% DMSO. Therefore DMSO was used as a negative control. The final DMSO concentration, in each well, was less than 0.1%. The cancer cells were treated with platinum complexes of compounds 1-7 and cisplatin, and the resulting cultures were incubated for 72 h. The medium of wells was discarded and 100 µL DMEM containing (5 mg/mL) MTT (3-(4,5-dimethylthiazol-2-yl)-2,5-diphenyltetrazolium bromide) was added to each well and the cultures incubated in a $CO_2$ incubator at 37° C. in the dark for 4 hrs. After incubation, a purple colored formazan (artificial chromogenic dye, a product of the reduction of water insoluble tetrazolium salts e.g., MTT by dehydrogenases and reductases) in the cells is produced and appeared as dark crystals in the bottom of the wells. The medium of culture was discarded from each well carefully to avoid disruption of the monolayer. Isopropanol (100 µL) was added in each well. The solution was thoroughly mixed in the wells to dissolve the formazan crystals which results in a purple solution. The absorbance of the 96-well plate was measured at 570 nm with Mithras 2LB943 multimode microplate reader against reagent blank.

Instrumentation:
Elemental analyses of the complexes were carried out on Perkin Elmer series II (CHNS/O) Analyzer 2400. The Infrared spectra of selenone ligands and their platinum(II) complexes were recorded on a Nicolet 6700 FTIR spectrometer using KBr pellets from 4000 to 400 $cm^{-1}$. The NMR measurements were carried out in DMSO on a JEOL JNM-LA 500 NMR spectrometer at 297 K. The $^1H$ and proton-decoupled $^{13}C$ NMR spectra were recorded at frequencies of 500.00 MHz and 125.65 MHz respectively. The spectral conditions for $^{13}C$ NMR were; 32 K data points, 0.963 s acquisition time, 3.2 µs pulse delay and a 5.75 µs pulse width for $^1H$ NMR, and 32 K data points, 0.963 s acquisition time, 2.5 s pulse delay and a 5.12 µs pulse width. The chemical shifts were measured relative to TMS. The $^{77}Se$ NMR chemical shifts were recorded at 95.35 MHz relative to an external reference ($SeO_2$ in $D_2O$) at 0.00 ppm, using 2.0 s pulse delay and using 0.311 s acquisition time.

Example 2

Synthesis of the platinum(II) complexes:

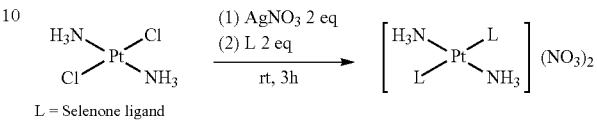

L = Selenone ligand

The platinum(II) complexes of selenone 1-7 (see FIG. 1) were prepared according to the equation above. In a typical synthesis, 0.17 g (1 mmol) of $AgNO_3$ was added to a solutions containing 0.15 g (0.5 mmol) of trans-diamminedichloridoplatinum(II) in 10 mL water and the mixture was stirred for one hour at room temperature. The solution was filtered to remove the precipitated silver chloride. Then, a selenone ligand (1.0 mmol) dissolved in 10 mL ethanol or acetonitrile was added to the filtrates drop wise. Stirring the solutions for one hour resulted in colored solution. The solution was filtered and kept at room temperature. Except in the case of PrImse complex, all complexes were solid powders isolated by slow evaporation of the solvent, Crystals of compound 5, trans-[Pt($NH_3$)$_2$(PrImSe)$_2$]($NO_3$)$_2$, were obtained. The elemental (MN) analysis data of the complexes Selenourea (Seu, 1), N,N'-dimethylselenourea ($Me_2$Seu, 2), 1,3-Imidazolidine-2-selenone (ImSe, 3), N-ethylimidazolidine-2-selenone (EtImSe, 4), N-propylimidazolidine-2-selenone (PrIMSe, 5), N-(i-propyl)imidazolidine-2-selenone (i-PrImSe, 6), and 1,3-Diazepane-2-selenone (DiapSe, 7) are listed in Table 1 (see FIG. 1 for the chemical structure of the selenone of compounds 1-7).

TABLE 1

Elemental analysis and melting points of trans-diammineplatinum(II) complexes of selenones, trans-[Pt($NH_3$)$_2$(selenone)$_2$]$NO_3$)$_2$

| Complex | Found (Calcd) % | | | M.P. (° C.) | Color |
| --- | --- | --- | --- | --- | --- |
| | C | H | N | | |
| [Pt($NH_3$)$_2$(Seu)$_2$]($NO_3$)$_2$ (1) | 3.92 (4.01) | 2.40 (2.35) | 17.97 (18.70) | 150-155 | Black |
| [Pt($NH_3$)$_2$($Me_2$Seu)$_2$]($NO_3$)$_2$ (2) | 10.80 (10.99) | 3.29 (3.38) | 17.47 (17.09) | 137-142 | Gray |
| [Pt($NH_3$)$_2$(ImSe)$_2$]($NO_3$)$_2$ (3) | 10.87 (11.06) | 2.88 (2.78) | 16.72 (17.20) | 180-185 | Black |
| [Pt($NH_3$)$_2$(EtImSe)$_2$]($NO_3$)$_2$ (4) | 16.70 (16.97) | 3.60 (3.70) | 16.07 (15.84) | 105-110 | Brown |
| [Pt($NH_3$)$_2$(PrImSu)$_2$]($NO_3$)$_2$ (5) | 19.74 (19.59) | 4.33 (4.11) | 15.44 (15.23) | 225-230 | White |
| [Pt($NH_3$)$_2$(i-PrImSu)$_2$]($NO_3$)$_2$ (6) | 20.06 (19.59) | 3.99 (4.11) | 14.94 (15.23) | — | White |
| [Pt($NH_3$)$_2$(DiapSe)$_2$]($NO_3$)$_2$ (7) | 16.75 (16.97) | 4.05 (3.70) | 15.77 (15.84) | 185-190 | Yellow |

Example 3

X-Ray Structure Determination:
The crystal data for complex 5 was collected at 293 K on a Stoe Mark II-Image Plate Diffraction System [Stoe & Cie. X-Area & X-RED32. Stoe & Cie GmbH, Darmstadt, Germany. 2009] equipped with a two-circle goniometer using MoKα graphite monochromatic radiation (λ=1.54184 Å). The structure was solved by direct methods with SHELX-97 [G. M. Sheldrick, Acta Cryst. 2008, A64, 112-122]. The refinement and all further calculations were carried with SHELX-2014 [G. M. Sheldrick. Acta Cryst. 2015, C71, 3-8]. The N—H hydrogen atoms were located in a difference Fourier map and refined with distance restraints: N—H=0.87(2) Å with 1.2 $U_{eq}$(N). The H-atoms bonded to carbon were included in the calculated positions and treated as riding atoms: C—H=0.97-0.98 Å with $U_{iso}$(H)=0.5 $U_{eq}$(C) for methyl groups H atoms, and =1.2 $U_{eq}$(C) for other H-atoms. The non-H atoms were refined anisotropically, using weighted full-matrix least-squares on $F^2$. A semi-empirical absorption correction was applied using the MULABS routine in PLATON [A. L. Spek. Acta Cryst. 2009, D65, 148-155]. The crystal data and details of refinement are given in Table 2.

TABLE 2

Crystal data and details of the refined structure for complex 5.

| Parameter | Value |
|---|---|
| Empirical formula | $C_{12}H_{30}N_8O_6PtSe_2$ |
| Formula weight | 735.45 |
| Crystal system | Triclinic |
| Space group | P-1 |
| a, b, c (Å) | 6.7486 (4), 7.0524 (4), 12.0717 (7) |
| α, β, γ (°) | 79.874 (5), 80.290 (5), 78.835 (5) |
| Cell volume (Å$^3$) | 549.47 (6) |
| $ρ_{calc}$, g/cm$^3$ | 2.223 |
| Z | 1 |
| F(000) | 352 |
| μ (mm$^{-1}$) | 16.14 |
| Wave λ (CuKα), Å | 1.54184 |
| Temperature, K | 293 |
| 2 theta range | 3.756-62.470 |
| h, k, l limits | −7:7, −8:8, −13:13 |
| Tmin, Tmax | 0.270, 1.000 |
| Reflns: Total, uniq. data, observed [I > 2σ(I)] | 6275, 1727, 1705 ($R_{int}$ = 0.0305) |
| Data, restraints, parameters | 1727, 0, 181 |
| $R_1$, $wR_2$, S [I > 2σ(I)] | 0.019, 0.050, 1.07 |
| $Δρ_{max}$, $Δρ_{min}$ (e Å$^{-3}$) | −0.84, 0.59 |

Program(s) used to refine structure: SHELXL2014 (Sheldrick, 2014).

Example 4

Spectroscopic Characterization of the Complexes:

Mixing of transplatin and selenones in a molar ratio of 1:2 in the presence of AgNO$_3$ in water yielded the complexes of the composition, [Pt(NH$_3$)$_2$(Selenone)$_2$](NO$_3$)$_2$].

(a) IR Spectroscopy

The significant IR bands, of the selenones and the platinum(II) complexes are listed in Table 3. The ν(C=Se) vibration that appears around 600 cm$^{-1}$ for free ligands shifted towards a lower frequency upon complexation similar to other complexes of selenone [Altoum et al. J. Coord. Chem. 70 (2017) 1020-1031; Altoum et al. Polyhedron, 128, 2-8 (2017); Ahmad et al. Polyhedron, 2002, 21, 2099-2105; S. Ahmad et al. J. Coord. Chem, 2003, 56, 539-544; and Isab et al. Polyhedron 25 (2006) 2629-2636, 49-511. The ν(N—H) and ν(C—N) bands were observed around 3200 cm$^{-1}$ and 1500 cm$^{-1}$ respectively. The appearance of these bands marks their coordination to the metal center. The absorptions near 800 and 1300 cm$^{-1}$ indicate the presence of nitrate ions [Isab et al. Polyhedron 29 (2010) 1251-1256; and Ahmad et al. Polyhedron 21 (2002) 1267].

TABLE 3

Selected IR absorptions (cm$^{-1}$) of selenones and their Pt(II) complexes

| Compound | ν(C=S) | ν(NH) | ν(C—N) | ν(NO)$_3$ |
|---|---|---|---|---|
| Seu | 736 | 3265 | 1520 | — |
| 1 | 606 | 3312, 3212 | 1404 | 1347 |
| Me$_2$Seu | 730 | 3245 | 1432 | — |
| 2 | 604 | 3365 | 1353 | 1351 |
| ImSe | 561 | 3250 | 1463 | — |
| 3 | 552 | 3293 | 1384 | 1363 |
| EtImSe | 514 | 3198 | 1465 | — |
| 4 | 561 | 3466 | 1383 | 1366 |
| PrImSe | 513 | 3210 | 1460 | — |
| 5 | 522 | 3312 | 1320 | 1375 |
| i-prImSe | 601 | 3210 | 1453 | — |
| 6 | 522 | 3350 | 1320 | 1387 |
| DiapSe | 615 | 3224 | 1453 | — |
| 7 | 600 | 3299 | 1324 | 1396 |

(B) NMR Spectroscopy

The $^1$H NMR chemical shifts of platinum(II) complexes in DMSO-d$_6$ are listed in the Table 4.

TABLE 4

$^1$H (for N—H proton), $^{13}$C {$^1$H} and $^{77}$Se{$^1$H} NMR chemical shifts of the Pt(II) complexes in DMSO-d$_6$

| Species | N—H | C = Se(1 | C-4 | C-5 | C-6 | N—C2 | N—C3 | δ ($^{77}$Se) |
|---|---|---|---|---|---|---|---|---|
| Seu | 7.59 | 178.8 | — | — | — | — | — | 200.7 |
| 1 | 8.47 | 169.2 | — | — | — | — | — | 155.6 |
| DmSeu | 7.53 | 177.8 | — | — | — | — | — | 231.4 |
| 2 | 8.39 | 168.1 | — | — | — | 45.4, | 46.7 | 198.5 |
| ImSe | 8.33 | 177.1 | — | — | — | 44.9 | 44.9 | 73.5 |
| 3 | 9.32 | 167.3 | — | — | — | 45.7 | 45.7 | 53.8 |
| EtImSe | 8.32 | 178.7 | 43.3 | 12.1 | — | 42.5 | 47.9 | 80.9 |
| 4 | 9.15 | 174.6 | 42.9 | 12.2 | — | 43.0 | 48.4 | 73.7 |
| PrImSe | 8.81 | 179.5 | 50.1 | 21.1 | 10.9 | 42.6 | 48.6 | 85.5 |
| 5 | 8.96 | 170.4 | 49.8 | 20.7 | 11.1 | 43.8 | 49.6 | 78.8 |
| i-PrImSe | 8.26 | 177.7 | 42.9 | 20.2 | — | 42.6 | 48.2 | 69.3 |
| 6 | 9.0 | 168.2 | 43.5 | 19.4 | — | 42.9 | 49.4 | 56.4 |
| DiapSe | 8.07 | 180.8 | 26.8 | — | — | 45.5 | 45.5 | 292.0 |
| 7 | 8.94 | 168.0 | 25.7 | — | — | 45.3 | 45.3 | 191.9 |

In proton NMR, the N—H hydrogen chemical shift of the complex is less intense and shifted downfield by 0.8 to 1.2 ppm from that of the free selenone compound. The shift was attributed to the shift of the electron density from nitrogen to carbon producing an increase in double bond character of the C—N bond. This downfield shift is characteristic of the selenones ligated to Pt(II) ion through the selenium atoms and not via a nitrogen atoms [Ahmad et al. Polyhedron, 21, 2099-2105 (2002); Ahmad et al. Inorg, Chem. Commun 5 (2002) 355; Ahmad et al. J. Coord. Chem., 2003, Vol. 56, No. 6, pp. 539-544; Isab et al. Polyhedron, 25, 2629-2636 (2006)].

The $^{13}$C {$^{1}$H} NMR chemical shifts for free selenones and their corresponding platinum complexes are summarized in Table 4. For all compounds, the selenocarbonyl (C=Se) resonance of selenone complexes shifted up field by 2.7 to 14 ppm relative to their positions in uncoordinated selenones, which is consistent with the previously reported observations [Ahmad et al. Polyhedron, 21, 2099-2105 (2002); Ahmed et al. Inorg. Chem. Commun. 5 (2002) 355; Ahmad et al. J. Coord. Chem., 2003, Vol. 56, No. 6, pp. 539-544; Isab et al. Polyhedron, 25, 2629-2636 (2006)]. The up field shift assigned for the C-2 resonance is due to decreasing C=Se bond order upon coordination concomitant with increasing the bond order of the carbon-nitrogen bond leading to increase in the double bond character in the C—N bond. The up field shifts imply that the coordination of selenones to Pt(II) ion occurs via selenium atom [Sadaf et al. Mol. Struc. 1085 (2015) 155-161; Ahmad et al. Polyhedron., 21, 2099-2105 (2002); Ahmad et al. Inorg. Chem. Commun. 5 (2002) 355; Ahmad et al. J. Coord. Chem., 2003, Vol. 56, No. 6, pp. 539-54)]. The increased electron density of the C—N bond upon coordination to platinum results in minor increases in deshielding effects on C-4 and C-5, as observed by downfield shifts in these resonances.

Example 5

Crystal Structure

Figure 2:
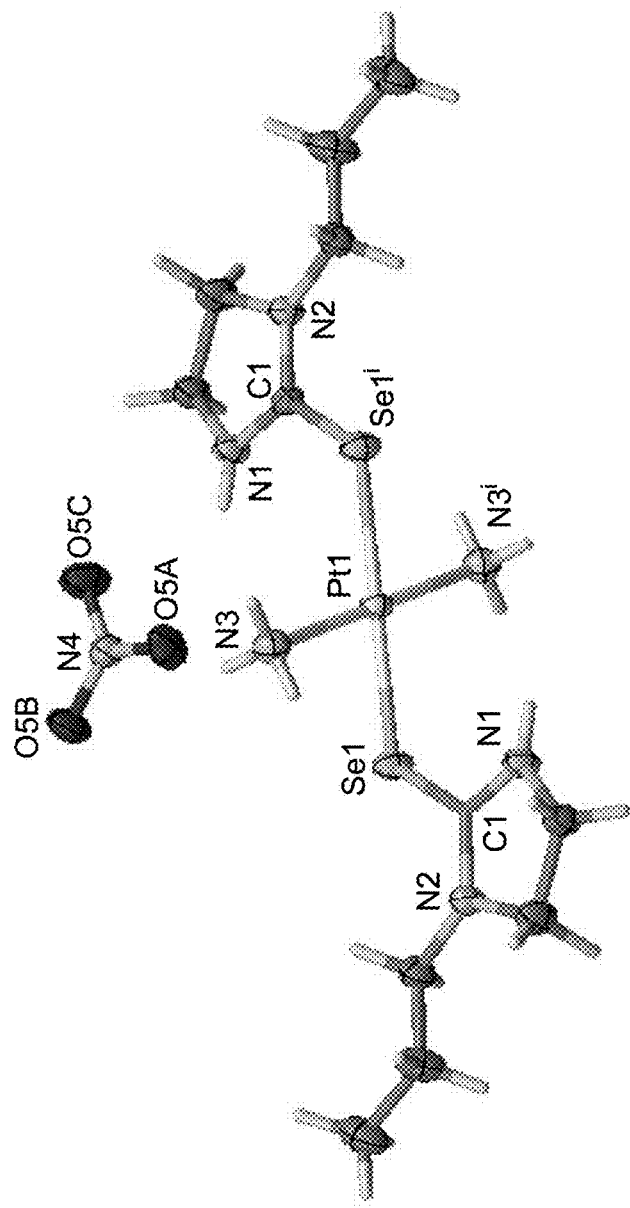
FIG. 2: Molecular structure of trans-[Pt(NH$_3$)$_2$(PrIm Se)$_2$](NO$_3$)$_2$ (5) with partial atom labelling and displacement ellipsoids drawn at the 50% probability level (no Ellipsoids shown).
Figure 3:
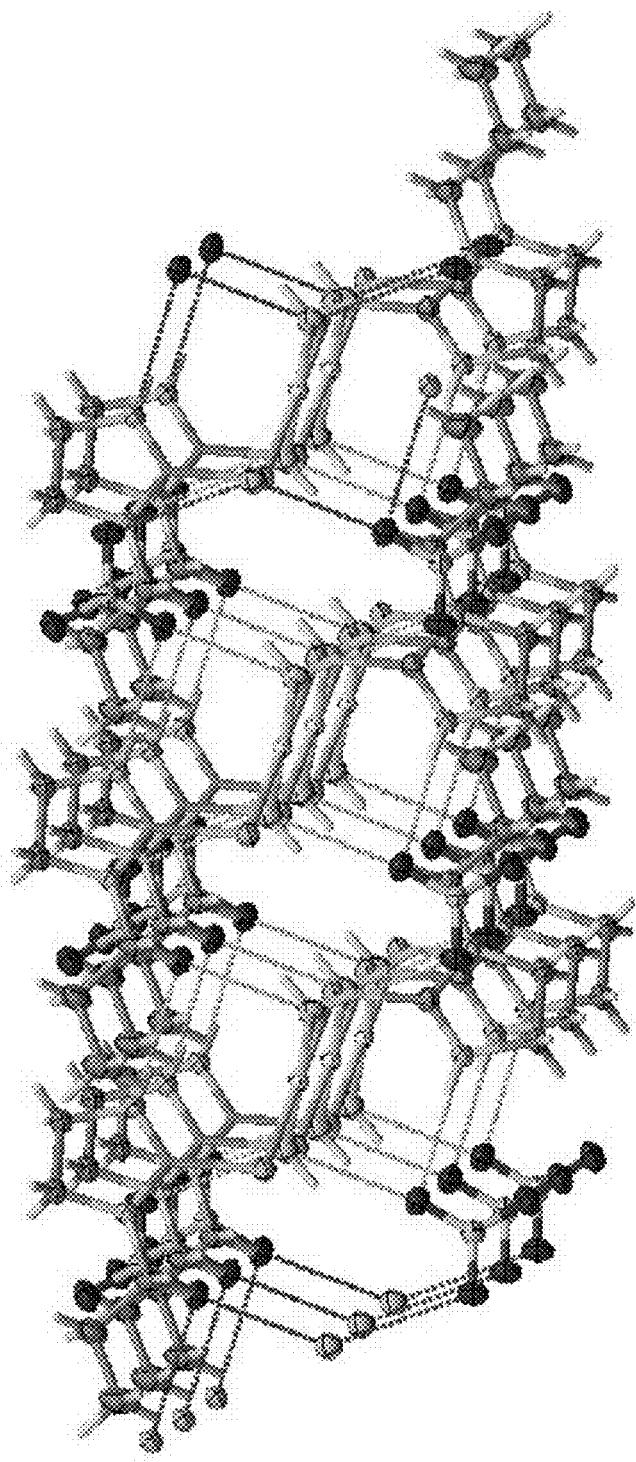
FIG. 3: The crystal packing of trans-[Pt(NH$_3$)$_2$(PrIm-Se)$_2$](NO$_3$)$_2$ (5) with hydrogen bonding (red and green labeling) viewed along the b axis.

The X-ray structure of compound 5 is shown in FIG. 2. The geometrical parameters are given in Table 2. The structure of 5 consists of a cationic complex, [Pt(NH$_3$)$_2$(PrImSe)$_2$]$^{2+}$ and two nitrate counter anions. In the complex ion, the platinum atom is bound to two N atoms of ammonia and two selenium atoms of N-ethylimidazolidine-2-selenone in a trans-configuration. The geometry of platinum complex is planar with the cis angles around platinum of 91.080(11) and 88.920(11), while the trans angles are 180°. The PtL$_4$ coordination unit is planar due to an inversion center at the Pt atom. The Pt—N and Pt—Se bond distances of 2.0440(3) and 2.4365(4) Å, respectively, are in agreement with the average values reported for other Pt complexes [Altoum et al. Polyhedron, 128, 2-8 (2017); Rani et al. Eur. J. Inorg. Chem. (2017) In press; Seerat-ur-Rehman et al. blocs. Chem. Commun. 36 (2013) 68-71; and Ahmad et al. Monatsh. Chem., 148 (2017) 669-674, each of which is incorporated herein by reference in its entirety. The SeCN$_2$ moieties of the selenone molecule are planar. The N—C(Se) bond length is smaller than that of the N—C(C) bond distance because of the marked increase of the double bond character of the N—C(Se) bond. In 5, the groups (N1-H1 and N3-H3 of selenone and ammonia ligands respectively) are engaged in hydrogen bonding with oxygen atoms of nitrate ions as shown in FIG. 2. The details of hydrogen-bond geometry (Å, °) in 5 are given in Table 5.

TABLE 5

Selected bond distances (Å) and bond angles (°) of compound 5

| Bond | Bond Distance Å | Bond angles | bond angles (°) |
|---|---|---|---|
| Pt1—Se1 | 2.4365(4) | Se1$^i$—Pt1—Se1 | 180.000(12) |
| Pt1—Se1$^i$ | 2.4365(4) | N3—Pt1—N3$^i$ | 180.000(14) |
| Pt1—N3 | 2.0440(3) | N3—Pt1—Se1$^i$ | 91.080(11) |
| Pt1—N3$^i$ | 2.0440(3) | N3—Pt1—Se1 | 88.920(11) |
| C1—Se1 | 1.8770(4) | N1—C1—Se1 | 125.800(3) |
| N1—C1 | 1.318(5) | N2—C1—Se1 | 122.400(3) |
| N1—C2 | 1.466(5) | N1—C1—N2 | 111.8(3) |

Symmetry codes, i: -x + 1, -y + 1, -z + 1

Example 5

Figure 4A:
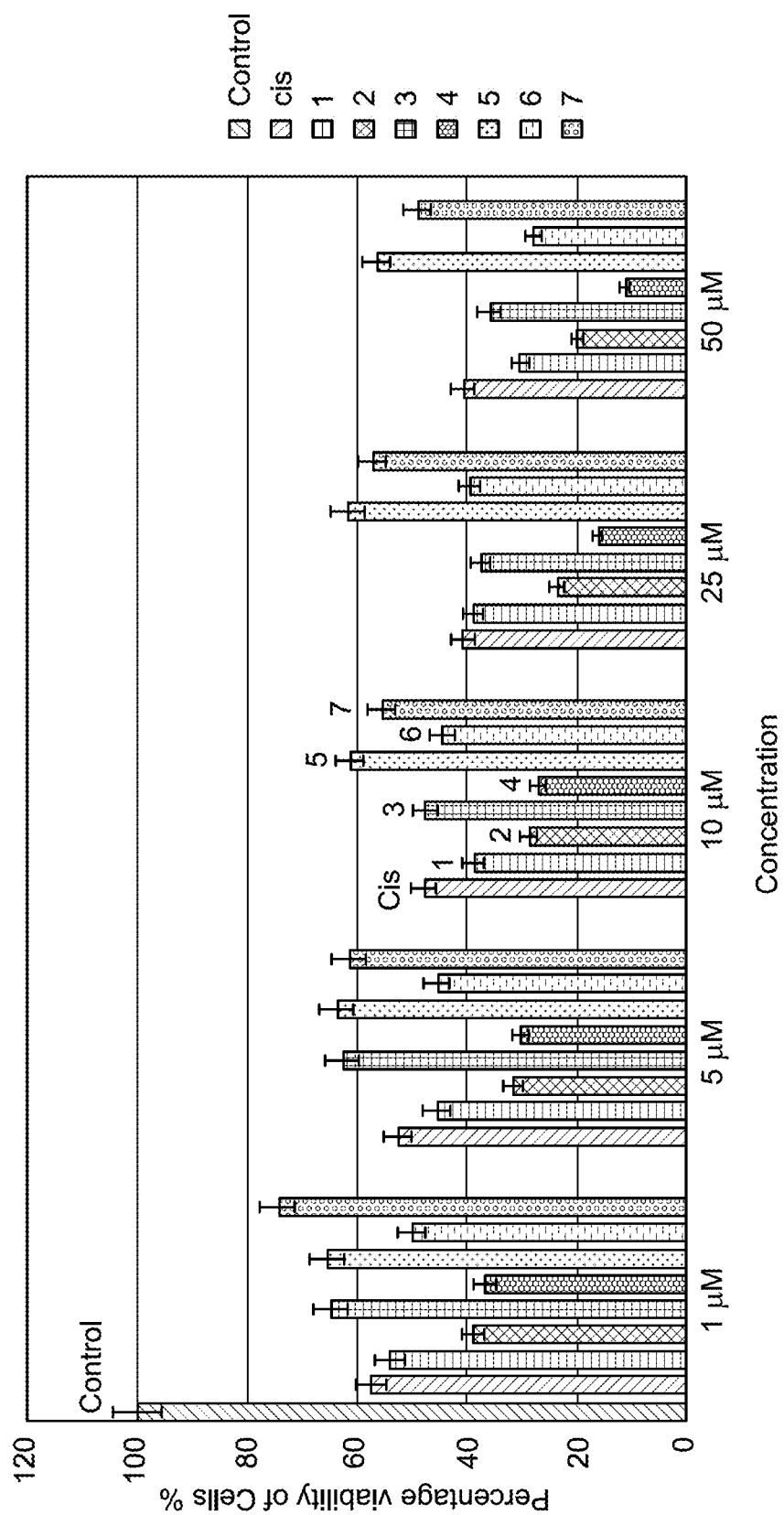
FIG. 4A: Effect of concentration of trans-[Pt(NH$_3$)$_2$(selenone)$_2$](NO$_3$)$_2$ complexes and cisplatin in on the percentage viability of HeLa cells.
Figure 4B:
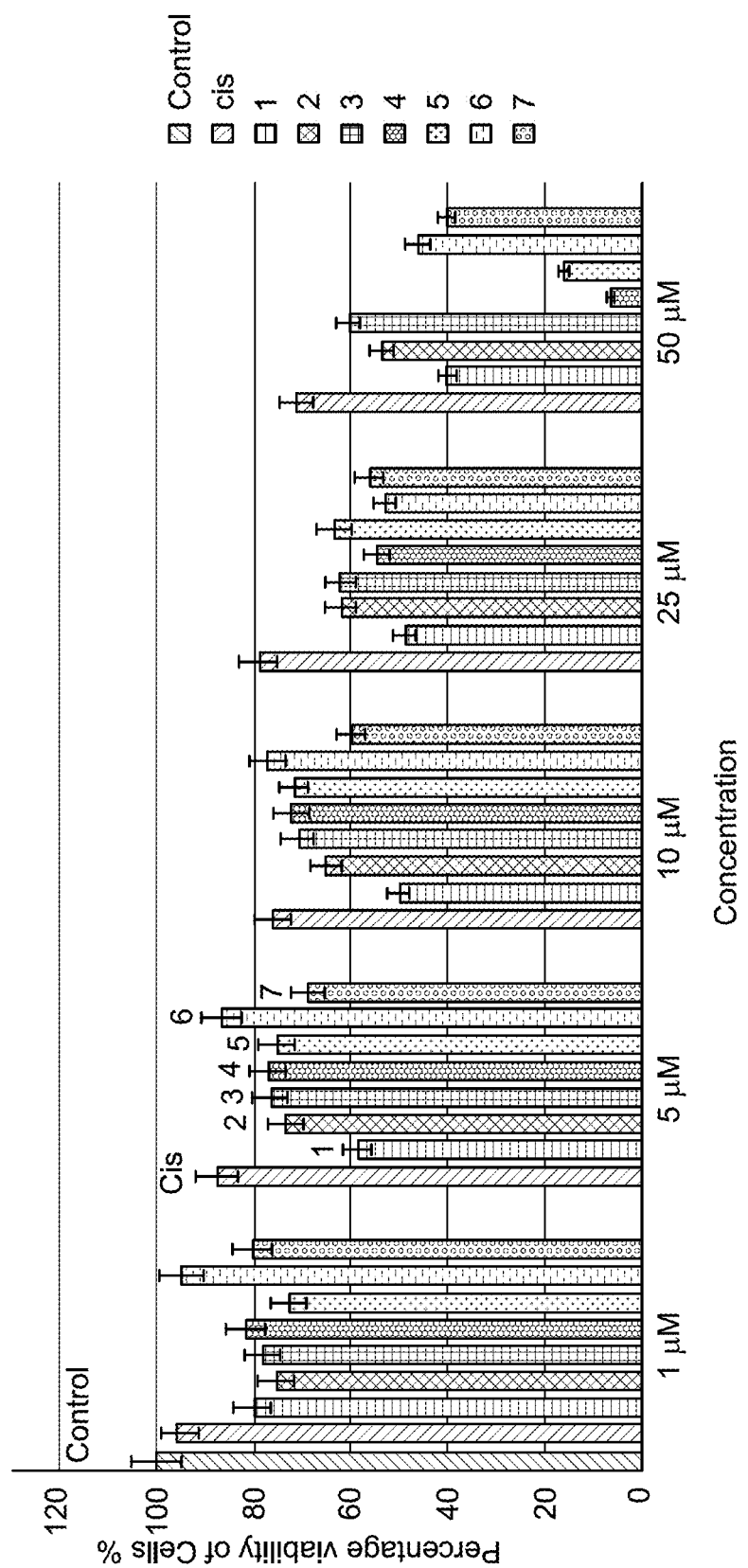
FIG. 4B: Effect of concentration of trans-[Pt(NH$_3$)$_2$(selenone)$_2$](NO$_3$)$_2$ complexes and cisplatin in on the percentage viability of MDA-231.

In Vitro Cytotoxicity:

In vitro cytotoxicity of the platinum complexes of compounds 1-7 and cisplatin it DMSO were evaluated by the MTT assay against two human cancer cells namely, human cervical cancer HeLa cells and human breast cancer MDA-231 cells. The results of cytotoxicity are expressed, in terms of IC$_{50}$ and listed m Table 7. The survival of the cells as a function of concentration of the platinum complexes of compounds 1-7 are graphically presented in FIGS. 4A and 4B. Compared to cisplatin, complexes of compounds 1, 4 and 6 display enhanced cytotoxicity in cell cultures of both Hela and MDA-321. Also, platinum complex of compound 2 is more cytotoxic than cisplatin with HeLa cells, whereas the complex of compound 3 exhibits comparable cytotoxicity. For MCF7 cell line, the complexes of compounds 5 and 8 have greater cytotoxicity than cisplatin, and the complexes of compound 2 and 3 are less active. Recently, the anticancer properties of some other platinum(II) complexes of heterocyclic selenones have been reported [Altoum et al J. Coord. Chem. 70 (2017) 1020-1031; and. Altoum et al. Polyhedron, 128, 2-8 (2017), 42]. They were found to possess high IC$_{50}$ values and thus, poor cytotoxicity as compared to cisplatin. The more effective antitumor properties of the current series may be ascribed to the presence of amine groups, to the ionic nature and to the different types of cancer cells

TABLE 7

IC$_{50}$ values (μM) of platinum(II) complexes (1-7) against HeLa and MDA-231 cancer cell lines

| Platinum Complex | HeLa | MDA-231 |
|---|---|---|
| Cisplatin | 3.6(±0.32) | 6.3(±0.11) |
| 1 | 3.1(±0.16) | 4.3(±0.11) |
| 2 | 2.3(±0.12) | 7.4(±0.06) |
| 3 | 3.7(±0.33) | 9.5(±0.13) |
| 4 | 2.1(±0.15) | 4.4(±0.2) |
| 5 | 6.9(±0.20) | 4.7(±0.15) |
| 6 | 3.1(±0.29) | 5.7(±0.16) |
| 7 | 5.4(±0.32) | 5.3(±0.12) |

The present disclosure describes the synthesis and characterization of trans-diammine platinum(II) complexes of heterocyclic selenones. The platinum complexes of the invention display in vitro anticancer activity against the human tumor cell lines HeLa and MDA-231 comparable to that of cisplatin.

The invention claimed is:
1. A platinum (II) complex having formula PtL$_2$(NH$_3$)$_2$$^{+2}$ X$^{-2}$, which is in a trans-configuration, wherein L has formula A

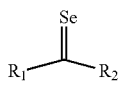

Formula A or a solvate thereof, a tautomer thereof, a stereoisomer thereof, or a mixture thereof;

wherein $R_1$ and $R_2$ are independently selected from the group consisting of a hydrogen, $NR_3R_4$, $OR_3$, $SR_3$, $SeR_3$, an optionally substituted alkyl, an optionally substituted alkylene, an optionally substituted cycloalkyl, an optionally substituted aryl, and an optionally substituted arylalkyl; and $R_3$ and $R_4$ are independently hydrogen, an optionally substituted alkyl, an optionally cycloalkyl, an optionally substituted heterocyclyl, an optionally substituted aryl, and an optionally substituted arylalkyl; or $R_1$ and $R_2$ are linked together forming an optionally substituted ring selected from the group consisting of a four membered ring, a five membered ring, a six membered ring, a seven membered ring, or an eight membered ring; and wherein $X^{-2}$ is two nitrate anions.

2. The platinum (II) complex of claim 1, wherein $R_1$ and $R_2$ are linked together forming the optionally substituted ring.

3. The platinum (II) complex of claim 1, wherein $R_1$ and $R_2$ are linked together to form a saturated or unsaturated cycloalkyl ring, or saturated or unsaturated heterocylic ring.

4. The platinum (II) complex of claim 1, wherein formula (A) is selected from the group consisting of:

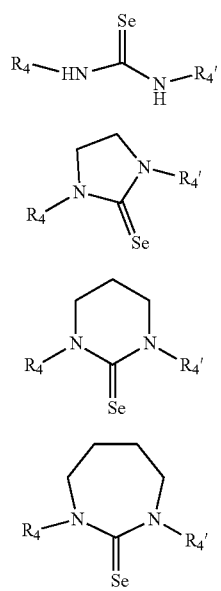

wherein $R_4$ and $R_{4'}$ are independently selected from the group consisting of hydrogen, methyl, ethyl, propyl, isopropyl, butyl, isobutyl, t-butyl, pentyl, isopentyl, phenyl, and benzyl.

5. A pharmaceutical composition comprising the platinum (II) complex of claim 4; and a pharmaceutically acceptable carrier and/or excipient.

6. A method for treating a proliferative disorder, comprising administering to a subject in need of therapy a sufficient amount of the pharmaceutical composition of claim 5, wherein the proliferative disorder is cancer.

7. The method of claim 6, wherein the cancer is at least one selected from the group consisting of ovarian cancer, cervical cancer, testicular cancer, colon cancer, bladder cancer, breast cancer, non-small cell lung cancer, esophageal cancer, endometrial cancer, head and neck cancer, and osteogenic sarcoma.

8. A method of making the platinum (II) complex of claim 1, said method comprising:
(a) mixing an aqueous solution of silver nitrate with an aqueous solution of trans-diaminedihaloplatinum(II) to form a silver chloride precipitate,
(b) filtering the precipitate and collecting the filtrate, and
(c) mixing a solution of a compound of formula A in a solvent miscible with water and the filtrate.

9. The method of claim 8, further comprising, after the mixing (c):
filtering the platinum (II) complex as a precipitate.

10. The method of claim 8, wherein the trans-diaminedihaloplatinum(II) is selected from the group consisting of trans-diaminedifluroplatinum(II), trans-diaminedichloroplatinum(II), trans-diaminedibromoplatinum(II), and trans-diaminediiodoplatinum(II).

11. A pharmaceutical composition comprising the platinum (II) complex of claim 1; and a pharmaceutically acceptable carrier and/or excipient.

12. The pharmaceutical composition of claim 11, which comprises 0.1-400 µM of the platinum (II) complex relative to the total volume of the composition.

13. The pharmaceutical composition of claim 11, wherein the pharmaceutically acceptable carrier and/or excipient is at least one selected from the group consisting of a buffer, an inorganic salt, a fatty acid, a vegetable oil, a synthetic fatty ester, a surfactant, and a polymer.

14. The pharmaceutical composition of claim 11, further comprising a chemotherapeutic agent.

15. A method for treating a proliferative disorder, comprising administering to a subject in need of therapy a sufficient amount of the pharmaceutical composition of claim 11, wherein the proliferative disorder is cancer.

16. The method of claim 15, wherein 1-300 mg/kg of the platinum (II) complex is administered per body weight of the subject.

17. The method of claim 15, wherein the cancer is at least one selected from the group consisting of ovarian cancer, cervical cancer, testicular cancer, colon cancer, bladder cancer, breast cancer, non-small cell lung cancer, esophageal cancer, endometrial cancer, head and neck cancer, and osteogenic sarcoma.

18. The method of claim 15, wherein the subject in need of therapy has a central nervous system tumor or a germ cell tumor.

19. The method of claim 15, wherein the subject is a mammal.

* * * * *